(12) United States Patent
Chang

(10) Patent No.: US 7,749,940 B2
(45) Date of Patent: Jul. 6, 2010

(54) FACILITATED FORWARD CHEMICAL GENETICS USING TAGGED TRIAZINE LIBRARY

(75) Inventor: Young-Tae Chang, New York, NY (US)

(73) Assignee: New York University, New York, NY (US)

( * ) Notice: Subject to any disclaimer, the term of this patent is extended or adjusted under 35 U.S.C. 154(b) by 110 days.

(21) Appl. No.: 10/838,911

(22) Filed: May 5, 2004

(65) Prior Publication Data

US 2005/0019831 A1 Jan. 27, 2005

Related U.S. Application Data

(60) Provisional application No. 60/467,598, filed on May 5, 2003.

(51) Int. Cl.
 *C40B 70/00* (2006.01)
(52) U.S. Cl. ............................. 506/41; 506/30; 506/15; 435/4
(58) Field of Classification Search ........................ None
 See application file for complete search history.

(56) References Cited

U.S. PATENT DOCUMENTS 6,207,826 B1 * 3/2001 Cook et al. ................. 540/472

FOREIGN PATENT DOCUMENTS

| WO | WO 99/37630 | * | 7/1999 |
| WO | WO 03/032903 A2 | | 4/2003 |
| WO | WO 03/050237 A2 | | 6/2003 |

OTHER PUBLICATIONS

Fivush et al. AMEBA: An acid sensitive aldehyde resin for solid phase synthesis. 1997 Tetrahedron Lett. 41:7151-7154.*
Crews, Craig and Ute Spittgerber, "Chemical Genetics: Exploring And Controlling Cellular Processes With Chemical Probes", TIBS, Trends in Biochemical Sciences, vol. 24, No. 8, Aug. 1, 1999, pp. 317-320.
Gustafson, et al, "Incorporation Of Carbohydrates And Peptides Into Large Triazine-Based Screening Libraries Using Automated Parallel Synthesis", TETRAHEDRON, vol. 54, 1998, pp. 4051-4065.
Khersonsky, et al, "Facilitated Forward Chemical Genetics Using A Tagged Triazine Library and Zebrafish Embryo Screening", J. Am. Chem. Soc., vol. 125, 2003, pp. 11804-11805.
Moon et al, "A Novel Microtubule Destabilizing Entity From Orthogonal Synthesis Of Triazine Library And Zebrafish Embryo Screening", J. Am. Chem. Soc., vol. 124, 2002, pp. 11608-11609.
Scharn, et al, "Spatially Addressed Synthesis Of Amino-And Amino-Oxy-Substituted 1,3,5-Triazine Arrays On Polymeric Membranes", J. Comb. Chem., vol. 2, 2000, pp. 361-369.
Schreiber,, Stuart, "Chemical Genetics Resulting From A Passion For Synthetic Organic Chemistry", Bioorganic & Medical Chemistry, vol. 6, 1998, pp. 1127-1152.
Silen, et al, "Screening for Novel Antimicrobials From Encoded Combinatorial Libraries by Using A Two-Dimensional Agar Format", Antimicrobial Agents and Chemotherapy, vol. 42, No. 6, Jun. 1998, pp. 1447-1453.

* cited by examiner

*Primary Examiner*—Christopher Low
*Assistant Examiner*—Christopher M Gross
(74) *Attorney, Agent, or Firm*—Browdy and Neimark PLLC

(57) ABSTRACT

A novel tagged triazine library is provided in which three building blocks are prepared separately and assembled orthogonally to yield 1536 highly pure compounds. Each library compound contains a variety of a triethyleneglycol (TG) linker at one of the diversity sites of the triazine scaffold.

4 Claims, 5 Drawing Sheets

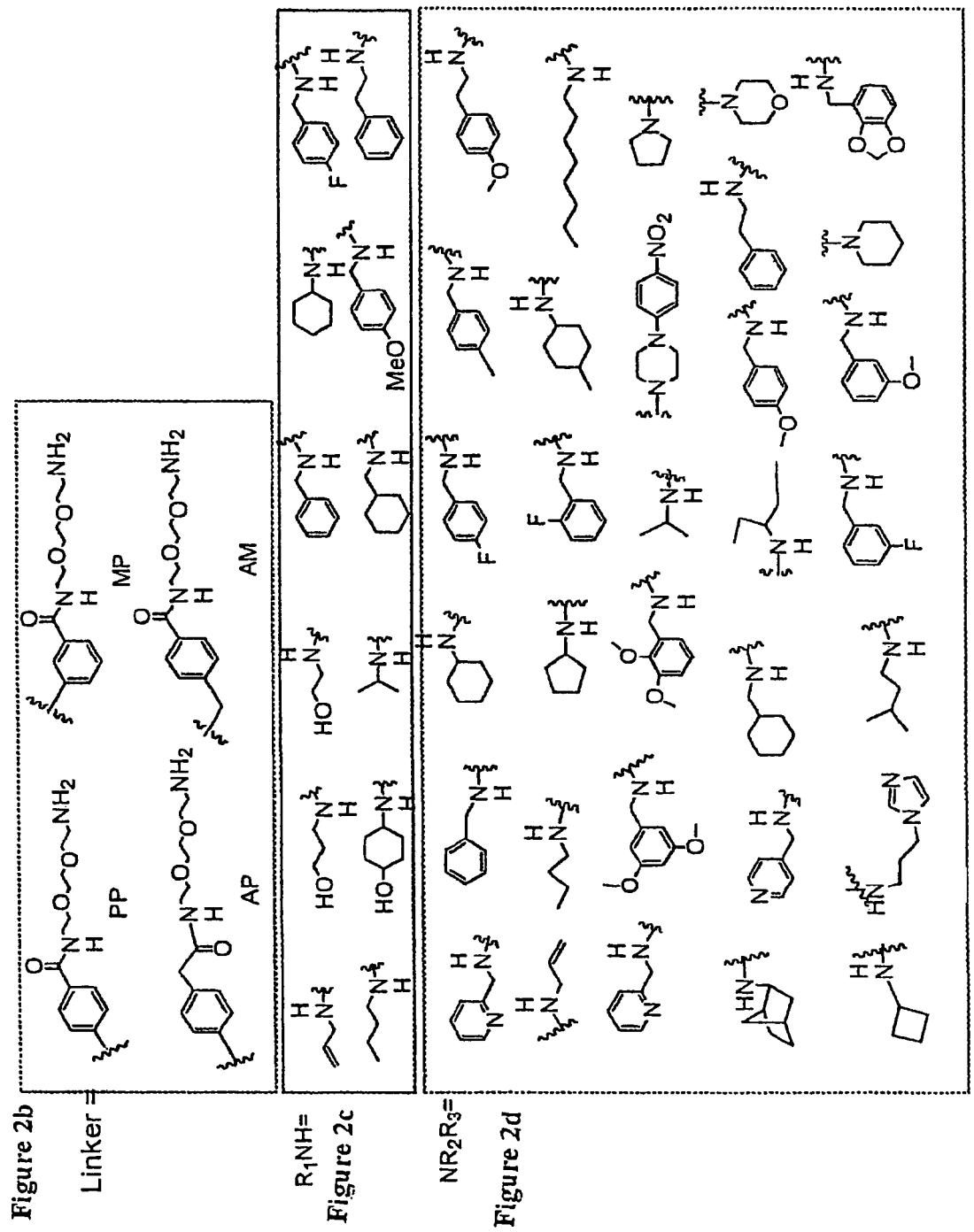
*Figure 2b* Linker =
*Figure 2c* R₁NH=
*Figure 2d* NR₂R₃=

FACILITATED FORWARD CHEMICAL GENETICS USING TAGGED TRIAZINE LIBRARY

CROSS-REFERENCE TO RELATED APPLICATIONS

This application claims priority from provisional application Ser. No. 60/467,598, filed May 5, 2003, the entire contents of which are hereby incorporated by reference.

FIELD OF THE INVENTION

The present invention is directed to the use of forward chemical genetics to evaluate triazine compounds.

BACKGROUND OF THE INVENTION

Forward chemical genetics is an emerging field that offers powerful tools to search for novel drug candidates and their targets (Lokey et al., 2002; Specht et al., 2002; Schreiber et al., 2003). Chemical genetics differs from classical genetics by substituting small molecules for mutation inducing agents or X-ray irradiation. Using combinatorial techniques (Jung, 1999; Nicolaou et al., 2002), one can rapidly screen a large number of small molecules and identify those that induce a novel phenotype in a cellular or embryonic system. Once a phenotype effect is found, the next step is to identify the biological target using an affinity matrix made of the immobilized hit compound. However, the synthesis of an efficient affinity matrix in which the hit compound does not lose activity has been shown to be challenging or sometimes totally impossible, because of the difficulties of attaching an adequate linker.

Traditionally, selected and modified active molecules, after biological screening, are fitted with a linker to provide for an attachment point to an affinity bead. In many cases, this can lead to loss of activity and thus a time consuming and laborious structure-activity relationship study (SAR) is required.

SUMMARY OF THE INVENTION

It is an object of the present invention to overcome the aforesaid deficiencies in the prior art.

It is another object of the present invention to provide a tagged library of triazine-based compounds.

It is a further object of the present invention to provide a systematic strategy for chemical genetics.

The present invention provides a targeted library based on a triazine scaffold. Triazine is a preferred scaffold because of its ease of manipulation and structural similarity to purine and pyrimidine, which have already been demonstrated to be active in various biological systems (Chang et al., 220; Verdugo et al., 2001; Armstrong et al., 2000; Rosania et al., 2000; Chang et al., 1999; Gangjee et al., 2003; Baraldi et al., 1998; Baraldi et al., 2002). In addition, the triazine scaffold has three-fold symmetry, and the positional modification is much more flexible than in the purines or pyrimidines.

The present inventor has previously described an orthogonal solid phase method to synthesize a triazine-based combinatorial library (Moon et al., 2002; Bork et al., 2003) and demonstrated anti-microtubule activities among the library entities (Moon et al., 2002).

The present invention provides a novel tagged triazine library in which three building blocks are prepared separately and assembled orthogonally to yield 1536 highly pure compounds. Each library compound contains a variety of a triethyleneglycol (TG) alkyl or aryl linker at one of the diversity sites of the triazine scaffold. The end group of the line carries azide, amino, NHBoc, biotin, acetylene or fluorescent compounds.

Incorporating the linkers in the compounds prior to biological screening provides a straightforward method for isolating the target protein without compromising the lead compound's activity of performing further SAR experiments.

Two possible problems may be envisioned. One is that the linker may interfere with biological activity and the active hits will be missed. However, this negative selection will be favorable for researchers, as it will reduce unfruitful efforts to modify the hit compounds later. The other possibility is that the linker itself may play an important role in the biological activity. However, this can easily be probed by detaching or modifying the linker. It should be noted that removing an already existing linker is much easier than adding a new one into the molecule via SAR.

The method of the present invention, in which three building bocks are prepared separately and assembled orthogonally, is shown in FIGS. 2a-2d. Incorporating a linker directly in the library compounds prior to phenotypic screening provides for a more efficient and elegant forward chemical genetics approach.

The tagged library system of the present invention is applied to biological systems to facilitate the general paradigm of forward chemical genetics.

BRIEF DESCRIPTION OF THE DRAWINGS

FIG. 1a shows synthesis of the linker library. FIG. 1b shows screening for a novel phenotype. FIG. 1c shows the affinity matrix step facilitated by a linker. FIG. 1d shows protein analysis and identification.

FIG. 2 is a scheme for synthesis of the linker libraries. FIG. 2b shows the linkers used. FIG. 2c shows amines and amino alcohols used for constructing building blocks I. FIG. 2d shows amines used for constructing building blocks III.

FIG. 3 is a scheme for solution phase synthesis of building blocks II.

DETAILED DESCRIPTION OF THE INVENTION

Incorporating linkers in a library of compounds prior to biological screening provides for a straightforward method for isolating a target protein without compromising the lead compound's activity or performing further SAR experiments.

The libraries produced by the present invention are useful in screening compounds in a biological assay in search for novel phenotypes and elucidating protein functions.

The linkers for use in the present invention comprise triethyleneglycol aryl or alkyl linkers. In order to provide detection capability, or to add labels for assays, the end group of the linker carries moieties such as azide, amino, NHBoc, biotin, acetylene, or fluorescent moieties.

For producing building block I, a primary amine or amino alcohol is used. The primary amine or amino alcohol may be a substituted or unsubstituted alkyl, alkenyl, alkynyl, or aryl primary amine or amino alcohol.

Figure 1:
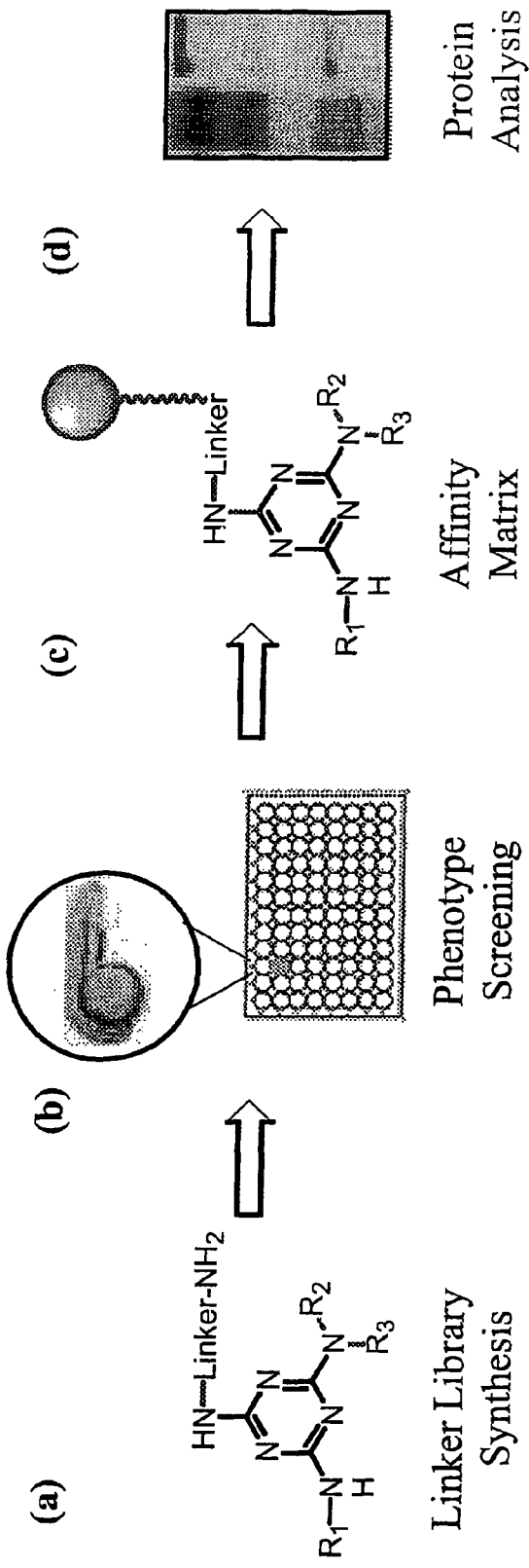
FIG. 1 shows a tagged library approach for chemical genetics.

The linker compound shown in FIG. 1a and the affinity matrix shown in FIG. 1c comprise a trisubstituted triazine substituted with R1, R2 and R3, which may be the same or different. R1, R2, and R3 can be substituted or unsubstituted aryl, alkyl, alkenyl, alkynyl, or cyclic or heterocyclic group.

As used herein, alkyl, alkenyl and alkynyl carbon chains, if not specified, contain from 1 to 20 carbon atoms, preferably from 1 to 16 carbon atoms, and are straight or branched. Alkenyl carbon chains of from 1 to 20 carbon atoms preferably contain 1 to 8 double bonds; the alkenyl carbon chains of 1 to 16 carbon atoms preferably contain from 1 to 5 double bonds.

Alkynyl carbon chains of from 1 to 20 carbon atoms preferably contain 1 to 8 triple bonds, and the alkynyl carbon chains of 1 to 16 carbon atoms preferably contain 1 to 5 triple bonds. The alkyl, alkenyl, and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms.

As used herein an alkyl group substituent includes halos, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "aryl" herein refers to aromatic cyclic compounds having up to 10 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused rings systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

"Cycloalkyl" as used herein refers to a saturated mono- or multicyclic ring system, preferably of 3 to 10 carbon atoms, more preferably from 3 to 6 carbon atoms. Cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged, or spiro-connected fashion, and may be optionally substituted with one or more alkyl group substituents.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The nomenclature alkyl, alkoxy, carbonyl, etc, is used as is generally understood by those of skilled this art. As used herein, aryl refers to saturated carbon chains that contain one or more carbon atoms; the chains may be straight or branched or include cyclic portions or may be cyclic.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "haloalkyl" refers to a lower alkyl radical in which one or more of the hydrogen atoms are replaced by halogen, including but not limited to, chloromethyl, trifluoromethyl, 1-chloro-2-fluoroethyl, and the like.

"Haloalkoxy" refers to RO— in which R is a haloalkyl group.

The term "sulfinyl" refers to —S(O)—. "sulfonyl" refers to —S(O)$_2$—.

"Aminocarbonyl" refers to —C(O)NH$_2$.

"Alkylene" refers to a straight, branched, or cyclic, preferably straight or branched, bivalent aliphatic hydrocarbon group, preferably having from 1 to about 20 carbon atoms. The alkylene group is optionally substituted with one or more alkyl group substituents. There may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to 6 carbon atoms. Preferred alkylene groups are lower alkylene, with alkylene of 1 to 3 atoms being particularly preferred.

The term "alkenylene" as used herein refers to a straight, branched or cyclic, preferably straight or branched, bivalent aliphatic hydrocarbon group, preferably having from about 1 to 20 carbon atoms and at least one double bond. The alkenylene group is optionally substituted with one or more alkyl group substituents. There may be optionally inserted along the alkenylene group one or more oxygen, sulfur, or substituted or unsubstituted nitrogen atoms, where the nitrogen substituent is alkyl as previously described.

As used herein, "alkynylene" refers to a straight, branched or cyclic bivalent aliphatic hydrocarbon group having from 1 to about 20 carbon atoms and at least one triple bond. The alkynylene group is optionally substituted with one or more alkyl group substituents. There may be optionally inserted along the alkynylene group one or more oxygen, sulfur, or substituted or unsubstituted nitrogen atoms, where the nitrogen substituent is alkyl. The term "lower alkynylene" refers to alkynylene groups having from 2 to 6 carbon atoms.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstituted nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents. As used herein, "alkylidene" refers to a bivalent group, such as =CR'R", which is attached to one atom of another group, forming a double bond. "Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

Figure 2A:
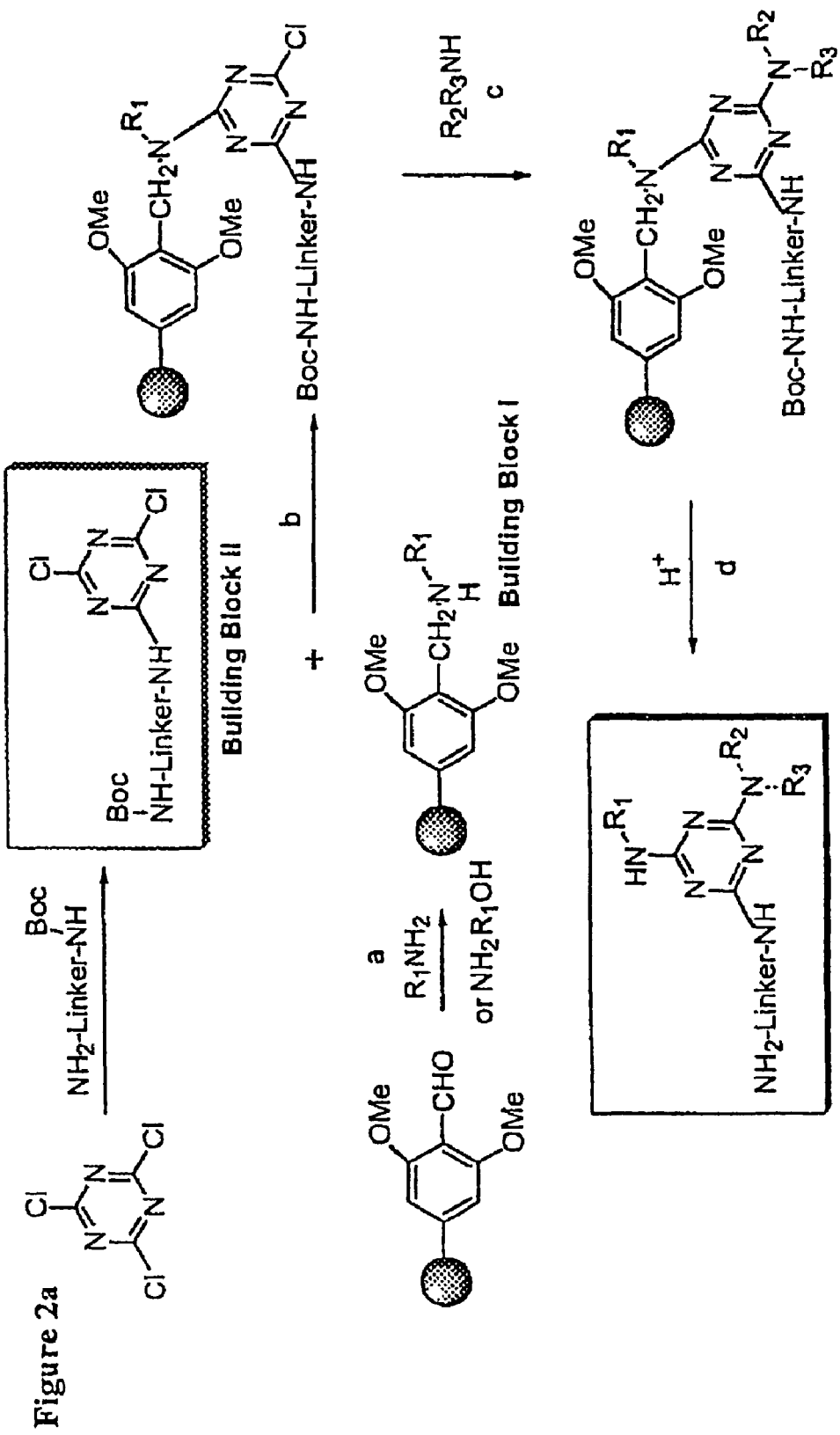
FIG. 2a is a general scheme for orthogonal synthesis reagents and conditions.

General Procedure for Building Block I Synthesis (FIG. 2)

The desired primary amine or amino alcohol is added to a suspension of a PAL aldehyde resin in anhydrous tetrahydrofuran (THF) containing 2% acetic acid at room temperature. The reaction mixture is shaken for one hour at room temperature, followed by addition of sodium triacetoxyborohydride. The reaction mixture is stirred for twelve hours and filtered. The resin is washed with N,N-dimethylformamide five times, alternatively with dichloromethane and methanol five times, and finally five times with dichloromethane. The resin was dried in vacuum.

Synthesis of Building Blocks II by Solution Phase Synthesis 2,2'-(ethylenedioxy)bis(ethylamine) was dissolved in dichloromethane and the solution cooled to 0° C. Di-tert-butyl-dicarbonate (Boc anhydride) was dissolved in dichloromethane and added to the solution of 2,2'-(ethylenedioxy)bis(ethylamine) dropwise over a period of three hours. The reaction mixture was allowed to stir for ten hours followed by extraction with saturated NaCl solution. The organic layers were combined and dried over $MgSO_4$. The solvent was removed in vacuo.

Figure 3A:
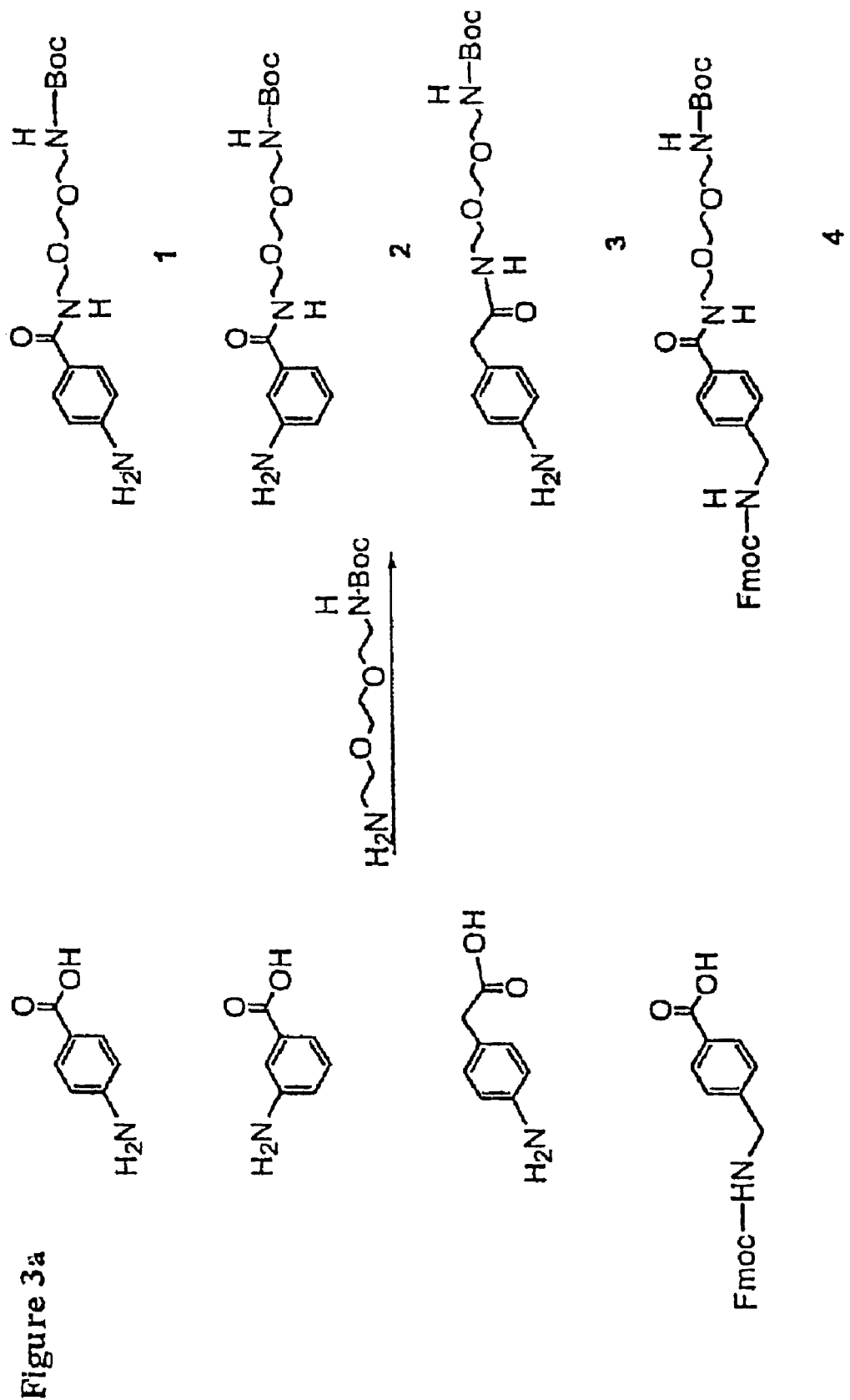
FIG. 3a shows DIC coupling of amino benzoic acids with a triethyleneglycol linker.

General DIC Coupling Procedure, Shown in FIG. 3a.

The appropriate amino benzoic acid was dissolved in DMF (except for Fmoc-aminomethylbenzoic acid, which was dissolved in THF) at room temperature. To the reaction mixture, 1-hydroxybenzo-triazole (HOBT) was added and allowed to stir for several minutes, followed by addition of 1,3-diisopropylcarboniimide (DIC) and allowed to stir for several minutes. Then, N-Boc-2,2'-(ethylenedioxy)bis(ethylamine) dissolved in either DMF, or THF in the case of N-Boc-2,2'-(ethylenedioxy)bis(ethylamine), was slowly added dropwise. The reaction mixture was allowed to stir overnight at room temperature. A solid DIC urea byproduct precipitated out of the reaction mixture, was filtered, and washed with ethyl acetate (EA). The filtrate was extracted three times with saturated aqueous sodium bicarbonate. The aqueous layer was back-extracted with ethyl acetate and saturated aqueous NaCl. The organic layers were combined and dried over $MgSO_4$. The solvent was removed in vacuo.

Figure 3B:
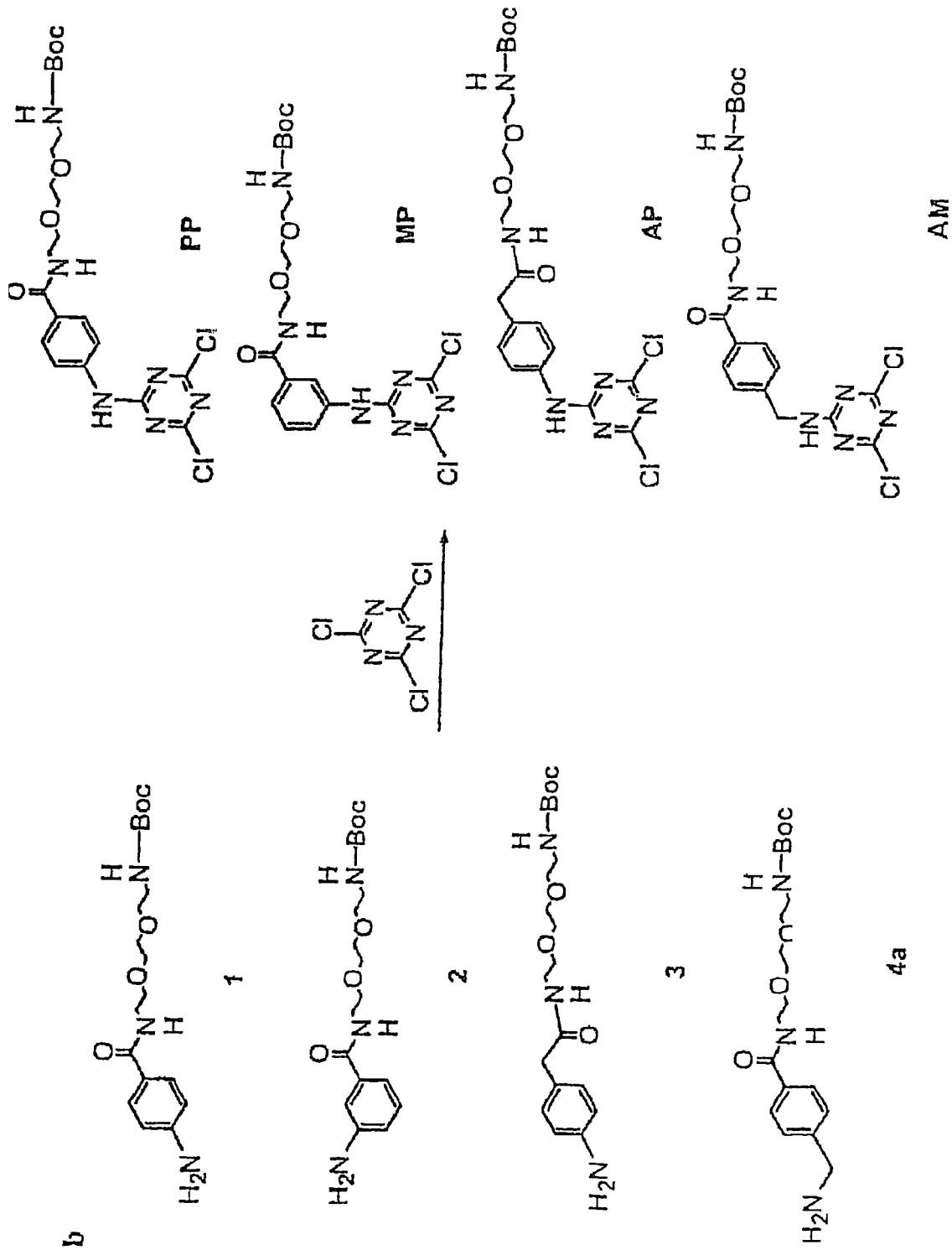
FIG. 3b shows coupling DIC intermediates to cyanuric trichloride to produce final Building Blocks II.

General Procedure for Coupling Cyanuric Trichloride to the DIC Intermediate (FIG. 3b)

Cyanuric chloride was dissolved in THF with DIEA at 0° C. Intermediate DIC coupled linker in THF was added dropwise. The reaction mixture was stirred and monitored by TLC. Reaction time was about 45 minutes to 1 hour. A solid precipitate slowly formed. Upon completion of the reaction, the reaction mixture was quickly filtered through a plug of flash silica and washed with ethyl acetate. The filtrate was evaporated in vacuo.

DIC Coupling of 4-Amino-benzoic Acid

The general DIC coupling procedure was followed and the compound 1 was purified using flash column chromatography (particle size 32-63 μm) using a gradient of 100% EA—10:1 EA:MeOH. TLC in EA ($R_f$ 0.22). The compound was identified by ESIMS: $(M+H)^+$ Calcd, 367.2; Found, 368.2. $H^1$ NMR (200 MHz, $CDCl_3$) δ 7.52 (d, 2H, J=7.6), 6.67 (s, 1H) 6.54 (d, 2H, J=8.5), 5.12 (s, 1H) 4.14 (s, 2H), 3.48 (m), 1.35 (s, 9H) Product was a viscous orange oil (87% yield).

Synthesis of [2-(2-{2-[4-(4,6-Dichloro-[1,3,5]triazin-2-ylamino)-benzoylamino]-ethoxy}-ethoxy)-ethyl]-carbamic Acid Tert-Butyl Ester (PP)

The general cyanuric chloride coupling procedure was followed for the intermediate linker 1. TLC conditions (100% EA $R_f$=0.36). The product was crystallized from a small amount of THF and EA with larger amounts of hexane. The product, PP, was filtered, washed with hexane, and dried under vacuum. PP was a white solid (37% yield). ESIMS: $(M+H)^+$ Calcd, 514.1; Found, 515.1. $H^1$ NMR (200 MHz, $CDCl_3$) δ11.35 (s, 1H), 8.51 (s, 1H), 7.9 (d, 2H, J=8.5 Hz), 7.7 (d, 2H, J=8.7 Hz), 6.78 (s, 1H) 3.4 (m), 3.0 (s, 2H), 1.37 (s, 9H).

DIC Coupling of 3-Amino-benzoic Acid

The general DIC coupling procedure was followed and the compound, 2 was purified using flash column chromatography (particle size 32-63 μm) using a gradient of dichloromethane:MeOH 35:1—dichloromethane:MeOH 20:1 EA. TLC in dichloromethane:MeOH 30:1 ($R_f$ 0.12) (68% yield). The compound was identified by ESIMS: $(M+H)^+$ Calcd, 367.2; Found, 368.2 and $H^1$ NMR (200 MHz, $CDCl_3$) δ7.0 (m, 3H) 6.8 (m, 1H), 5.22 (s, 1H), 3.4 (m), 3.2 (m, 2H) 1.36 (s, 9H).

Synthesis of [2-(2-{2-[3-(4,6-Dichloro-[1,3,5]triazin-2-ylamino)-benzoylamino]-ethoxy}-ethoxy)-ethyl]-carbamic acid tert-butyl ester (MP)

The general cyanuric chloride coupling procedure was followed for the intermediate linker 2. TLC conditions (100% EA $R_f$=0.43). The product was crystallized by evaporating the concentrated filtrate with THF and hexane. The re-concentrated reaction mixture was crystallized from 1:10 THF:ethyl ether. The product, MP, was filtered, washed with ether, and dried under vacuum. MP was a white solid (31% yield). ESIMS: (M+H)+ Calcd, 514.1; Found, 515.1. H$^1$ NMR (200 MHz, CDCl$_3$) δ 11.23 (s, 1H), 8.54 (s, 1H), 8.02 (s, 1H), 7.75 (m, 1H), 7.6 (m, 1H), 7.4 (m, 1H), 6.75 (s, 1H), 3.52-3.35 (m), 3.03 (m, 2H) 1.35 (s, 9H)

DIC Coupling of (4-Amino-phenyl)-acetic Acid

The general DIC coupling procedure was followed and the compound, 3, was purified using flash column chromatography (particle size 32-63 μm) using a gradient of dichloromethane:MeOH 35:1—dichloromethane:MeOH 25:1 EA. TLC in dichloromethane:MeOH 30:1 (R$_f$: 0.12) (77% yield). The compound was identified by ESIMS: (M+H)+ Calcd, 381.2; Found, 382.1 and H$^1$ NMR (200 MHz, CDCl$_3$) δ7.03 (d, 2H, J=6 MHz, 6.8 (d, 2H, 8.36 MHz, 6.0 (s, 1H) 5.15 (s, 1H) 3.75 (s, 2H) 3.4 (m) 1.86 (s, 2H) 1.45 (s, 9H).

Synthesis of {2-[2-(2-{2-[4-(4,6-Dichloro-[1,3,5]triazin-2-ylamino)-phenyl]-acetylamino}-ethoxy)-ethoxy]-ethyl}-carbamic Acid Tert-Butyl Ester (AP)

The general cyanuric chloride coupling procedure was followed for the intermediate linker 3. TLC conditions (100% EA R$_f$=0.25). The product, AP, was isolated using flash chromatography (particle size 32-63 μm) with a 100% EA—1:10 EA:MeOH gradient. AP is an off white solid (59% yield). ESIMS: (M+H)+ Calcd, 528.1; Found, 529.1. H$^1$ NMR (200 MHz, CDCl$_3$) δ 11.1 (s, 1H), 8.14 (s, 1.H) 7.5 (d, 2H, J=8.48), 7.26 (d, 2H, J=8.42) 3.4 (m), 3.2 (m, 2H) 3.1 (m, 2H) 1.36 (9H)

Synthesis of (N-Fmoc-4-aminomethyl)-benzoic Acid (4-aminomethyl)-benzoic acid (4.9 g, 1.1 equiv.) was dissolved in 5% NaHCO$_3$ 150 ml in water and stirred. N-(9-Fluorenylmethoxycarbonyl)-L-proline (Fmoc, 1 equiv., 10 g) was dissolved in an equivalent amount of dioxane and added. The reaction was allowed to stir at room temperature. After two hours, 10% citric acid in water 75 ml was added. A white solid precipitated upon addition. The solid was washed filtered and washed with hexane. The solid was dissolved in THF and allowed to dry overnight over MgSO$_4$. The following day, the solution was filtered, crystallized from THF and hexane, and placed under a drying vacuum (90% yield). ESIMS: (M+H)+ Calcd, 373.1; Found, 374.1.

DIC Coupling of {2-[2-(2-{4-[(9H-Fluoren-9-yl-methoxycarbonylamino)-methyl]-benzoylamino}-ethoxy)-ethoxy]-ethyl}-carbamic Acid Tert-Butyl Ester The general DIC coupling procedure was followed in THF, the compound, 4 was isolated using flash chromatography (particle size 32-63 μm) with 100% EA TLC (100% EA R$_f$: 0.23) (35% yield); ESIMS: (M+H)+ Calcd, 603.3; Found, 604.3. H$^1$ NMR (200 MHz, CDCl$_3$) 7.74-7.26 (m), 6.7 (s, 1H), 5.3 (s, 1H) 3.7-4.0 (m), 3.2 (m, 3H) 1.4 (s, 9H), 1.0 (s, 7H)

Fmoc Cleavage of 4

Fmoc cleavage was performed in 10% piperidine and dichloromethane with stirring at room temperature, the reaction progress was monitored by TLC. The reaction time was 2.5 hrs. The solvent was removed in vacuo. The compound, 4a was isolated using flash chromatography (particle size 32-63 μm) with a 100% EA—1:20 EA:MeOH (with 1% triethylamine) gradient (80% yield). ESIMS: (M+H)+ Calcd, 381.2; Found, 382.2.

Synthesis of {2-[2-(2-{4-[(4,6-Dichloro-[1,3,5]triazin-2-ylamino)-methyl]-benzoylamino}-ethoxy)-ethoxy]-ethyl}-carbamic Acid Tert-Butyl Ester (AM)

The general cyanuric chloride coupling procedure was followed for the intermediate linker 4a. (100% dichloromethane:Acetone R$_f$ 5:1=0.21) The product, AM was isolated using flash chromatography (particle size 32-63 μm) with a dichloromethane:Acetone 5:1—dichloromethane:Acetone 3:1 gradient. The product was an orange oil (52% yield). TLC (dichloromethane:acetone 5:1, R$_f$=0.21) ESIMS: (M+H)+ Calcd, 528.1; Found, 529.1. H$^1$ NMR (200 MHz, CDCl$_3$) δ 7.6-7.8 (d, 2H, J=4 Hz) 7.35-7.37 (d, 2H, 4 Hz), 6.7-6.8 (m, 2H) 4.9 (s, 1H), 4.72 (d, 2H, J=4 Hz,) 3.5-3.7 (m) 3.2 (m, 2H) 1.8 (s, 2H) 1.4 (s, 9H).

General Procedure for Coupling Building Block I and Building Block II

Building Block II (0.44 mmole) was added to Building Block I (0.11 mmole) in DIEA (1 mL) and anhydrous THF (10 mL) at room temperature. The reaction mixture was heated to 60° C. for 3 hr and filtered. The resin was washed with DMF (5 times), alternatively with dichloromethane and methanol (5 times), and finally dichloromethane (5 times). The resin was dried in vacuum.

General Procedure for the Final Amination on the Resin and Product Cleavage

Reaction

Desired amines (4 equiv.) were added to the resin (10 mg), coupled with Building Block I and Building Block II, in DIEA (8 μL) and 1 mL of NMP:n-BuOH (1:1). The reaction mixture was heated to 120° C. for 3 hr. The resin was washed with DMF (5 times), alternatively with dichloromethane and methanol (5 times), and finally dichloromethane (5 times). The resin was dried in vacuum.

The product cleavage reaction was performed using 10% trifluoroacetic acid (TFA) in dichloromethane (1 mL) for 30 min at room temperature and washed with dichloromethane (0.5 mL).

Free hydroxyl containing compounds were further treated with a piperazine resin in 0.5 ml THF at room temperature for 5 hrs to cleave the trifluoroacetic ester that was formed upon treatment with TFA. The resin was filtered out and washed with 0.1 ml THF.

The purity and identity of all the products were monitored by LC-MS at 250 nm (Agilent 1100 model); more than 90% of compounds demonstrated >90% purity.

Materials Used

Unless otherwise noted, materials and solvents were obtained from commercial suppliers (Acros and Aldrich) and were used without further purification. PAL-aldehyde (4-formyl-3,5-dimethoxyphenoxymethyl) resin from Midwest Bio-Tech (Cat #: 20840, Lot #: SY03470, loading level 1.10 mmole/g) was used for the generation of library compounds. Building Block II compounds, made by solution phase chemistry, were purified by flash column chromatography on Merck silca gel 60-PF254. All library products were identified by an LC-MS at 250 nm (Agilent Technology, HP1100) using a C18 column (20×4.0 mm) with a gradient of 5-95% CH$_3$CN—H$_2$O (containing 0.1% acetic acid) as an eluant over 4 min. Thermal libraries were synthesized using a Standard heat block from VWR Scientific Products using 4 ml glass vials with paper-lined caps purchased from Fisher Scientific. Resin filtration procedures were carried out using a 70μ PE frit cartridges from Applied Separations (cat. # 2449).

Affi-gel-10 was purchased from BioRad. EDTA, EGTA, Glycine, NaF, phenylmethylsulfonylfluoride (PMSF) and Trizma base were from Sigma Chemicals. Silver Stain Kit and pre-casted tris-glycine gel were obtained from Invitrogen. Protein inhibitor cocktail was purchased from Roche. Nonidet P-40 was from Fluka.

General Procedure for Building Block I Synthesis

The desired primary amine or amino alcohol (2.8 mmole, 5 equiv.) was added to a suspension of the PAL aldehyde resin (1.3 g, 1.43 mmole) in anhydrous tetrahydrofuran (THF) (50 mL containing 2% of acetic acid) at room temperature. The reaction mixture was shaken for 1 hr at room temperature followed by addition of sodium triacetoxyborohydride (2.1 g, 9.9 mmole, 7 equiv.). The reaction mixture was stirred for 12 hr and filtered. The resin was washed with N,N-dimethylformamide (DMF) (5 times), alternatively with dichloromethane and methanol (MeOH) (5 times), and finally with dichloromethane (5 times). The resin was dried in vacuum.

Synthesis of Building Blocks II by Solution Phase Synthesis

Synthesis of N-Boc-2,2'-(Ethylenedioxy)bis(ethylamine)(TG-Boc)

2,2'-(Ethylenedioxy)bis(ethylamine) (10 equiv.) was dissolved in dichloromethane and solution was cooled down to 0° C. Di-tert-butyl dicarbonate (Boc anhydride) (1 equiv.) was dissolved in dichloromethane and added to the solution of 2,2'-(Ethylenedioxy)bis(ethylamine) dropwise over a period of 3 hours. The reaction mixture was allowed to stir for 10 hours followed by extraction with saturated NaCl solution. The organic layers were combined and dried over $MgSO_4$. The solvent was removed in vacuo (64% yield).

General DIC Coupling Procedure

The appropriate amino benzoic acid (3 equiv.) was dissolved in DMF (except for Fmocaminomethylbenzoic acid which was dissolved in THF) at room temperature. To the reaction mixture, 1 equiv. of 1-hydroxybenzo-triazole (HOBT) was added and allowed to stir for several minutes followed by 1,3-diisopropylcarboniimide (DIC, 6 equiv.) and allowed to stir for several minutes. Then, N-Boc-2,2'(Ethylenedioxy)bis(ethylamine) dissolved in either DMF, or THF in the case of Fmoc-aminomethylbenzoic acid, was slowly added drop-wise. The reaction mixture was allowed to stir overnight at room temperature. A solid DIC urea byproduct precipitated out of the reaction mixture was filtered and washed with ethyl acetate (EA). The filtrate was extracted (3×10 times the volume of saturated sodium bicarbonate ($NaHCO_3$) in water). The aqueous layer was back-extracted with EA and sat. NaCl in water. The organic layers were combined and dried over $MgSO_4$. The solvent was removed in vacuo.

General Procedure for Coupling of Cyanuric Trichloride to the DIC Intermediate

Cyanuric chloride (1 equiv.) was dissolved in THF with DIEA (10 equiv.) at 0° C. Intermediate DIC coupled linker (1.2) equiv. in THF was added dropwise. The reaction mixture was stirred and monitored by TLC. Reaction time was 45 min. to 1 hr. A solid precipitate slowly formed. Upon completion of the reaction, the reaction mixture was quickly filtered through a plug of flash silica and washed with EA. The filtrate was evaporated in vacuo.

DIC Coupling of 4-Amino-benzoic Acid

The general DIC coupling procedure was followed and the compound 1 was purified using flash column chromatography (particle size 32-63 μm) using a gradient of 100% EA—10:1 EA:MeOH. TLC in EA (Rf: 0.22). The compound was identified by ESIMS: (M+H)+ Calcd, 367.2; Found, 368.2. $H^1$ NMR (200 MHz, $CDCl_3$) δ 7.52 (d, 2H, J=7.6), 6.67 (s, 1H) 6.54 (d, 2H, J=8.5), 5.12 (s, 1H) 4.14 (s, 2H), 3.48 (m), 1.35 (s, 9H) Product was a viscous orange oil (87% yield).

Synthesis of [2-(2-{2-[4-(4,6-Dichloro-[1,3,5]triazin-2-ylamino)-benzoylamino]-ethoxy}-ethoxy)-ethyl]-carbamic Acid Tert-Butyl Ester (PP)

The general cyanuric chloride coupling procedure was followed for the intermediate linker 1. TLC conditions (100% EA $R_f$=0.36). The product was crystallized from a small amount of THF and EA with larger amounts of hexane. The product, PP, was filtered, washed with hexane, and dried under vacuum. PP was a white solid (37% yield). ESIMS: (M+H)+ Calcd, 514.1; Found, 515.1. $H^1$ NMR (200 MHz, $CDCl_3$) δ 11.35 (s, 1H), 8.51 (s, 1H), 7.9 (d, 2H, J=8.5 Hz), 7.7 (d, 2H, J=8.7 Hz), 6.78 (s, 1H) 3.4 (m), 3.0 (s, 2H), 1.37 (s, 9H).

DIC Coupling of 3-Amino-benzoic Acid

The general DIC coupling procedure was followed and the compound, 2 was purified using flash column chromatography (particle size 32-63 μm) using a gradient of dichloromethane:MeOH 35:1—dichloromethane:MeOH 20:1 EA. TLC in dichloromethane:MeOH 30:1 ($R_f$: 0.12) (68% yield). The compound was identified by ESIMS: (M+H)+ Calcd, 367.2; Found, 368.2 and $H^1$ NMR (200 MHz, $CDCl_3$) δ 7.0 (m, 3H) 6.8 (m, 1H), 5.22 (s, 1H), 3.4 (m), 3.2 (m, 2H) 1.36 (s, 9H).

Synthesis of [2-(2-{2-[3-(4,6-Dichloro-[1,3,5]triazin-2-ylamino)-benzoylamino]-ethoxy}-ethoxy)-ethyl]-carbamic Acid Tert-Butyl Ester (MP)

The general cyanuric chloride coupling procedure was followed for the intermediate linker 2. TLC conditions (100% EA $R_f$=0.43) The product was crystallized by evaporating the concentrated filtrate with THF and hexane. The re-concentrated reaction mixture was crystallized from 1:10 THF:ethyl ether. The product, MP, was filtered, washed with ether, and dried under vacuum. MP was a white solid (31% yield). ESIMS: (M+H)+ Calcd, 514.1; Found, 515.1. $H^1$ NMR (200 MHz, $CDCl_3$) δ 11.23 (s, 1H), 8.54 (s, 1H), 8.02 (s, 1H), 7.75 (m, 1H), 7.6 (m, 1H), 7.4 (m, 1H), 6.75 (s, 1H), 3.52-3.35 (m), 3.03 (m, 2H) 1.35 (s, 9H).

DIC Coupling of (4-Amino-phenyl)-acetic Acid

The general DIC coupling procedure was followed and the compound, 3, was purified using flash column chromatography (particle size 32-63 μm) using a gradient of dichloromethane:MeOH 35:1—dichloromethane:MeOH 25:1 EA. TLC in dichloromethane:MeOH 30:1 ($R_f$: 0.12) (77% yield). The compound was identified by ESIMS: (M+H)+ Calcd, 381.2; Found, 382.1 and $H^1$ NMR (200 MHz, $CDCl_3$) δ 7.03 (d, 2H, J=6 MHz), 6.8 (d, 2H, 8.36 MHz), 6.0 (s, 1H) 5.15 (s, 1H) 3.75 (s, 2H) 3.4 (m) 1.86 (s, 2H) 1.45 (s, 9H).

Synthesis of {2-[2-(2-{2-[4-(4,6-Dichloro-[1,3,5] triazin-2-ylamino)-phenyl]-acetylamino}-ethoxy)-ethoxy]-ethyl}-carbamic Acid Tert-Butyl Ester (AP)

The general cyanuric chloride coupling procedure was followed for the intermediate linker 3. TLC conditions (100% EA $R_f$=0.25). The product, AP, was isolated using flash chromatography (particle size 32-63 μm) with a 100% EA—1:10 EA:MeOH gradient. AP is an off white solid (59% yield). ESIMS: (M+H)+ Calcd, 528.1; Found, 529.1 $H^1$ NMR (200 MHz, $CDCl_3$) δ 11.1 (s, 1H), 8.14 (s, 1.H) 7.5 (d, 2H, J=8.48), 7.26 (d, 2H, J=8.42) 3.4 (m), 3.2 (m, 2H) 3.1 (m, 2H) 1.36 (9H).

Synthesis of (N-Fmoc-4-aminomethyl)-benzoic Acid (4-aminomethyl)-benzoic acid (4.9 g, 1.1 equiv.) was dissolved in 5% $NaHCO_3$ 150 ml in water and stirred. N-(9-Fluorenylmethoxycarbonyl)-L-proline (Fmoc, 1 equiv., 10 g) was dissolved in an equivalent amount of dioxane and added. The reaction was allowed to stir at room temperature. After two hours, 10% citric acid in water 75 ml was added. A white solid precipitated upon addition. The solid was washed filtered and washed with hexane. The solid was dissolved in THF and allowed to dry overnight over $MgSO_4$. The following day, the solution was filtered, crystallized from THF and hexane, and placed under a drying vacuum (90% yield). ESIMS: (M+H)+ Calcd, 373.1; Found, 374.1.

DIC Coupling of {2-[2-(2-{4-[(9H-Fluoren-9-yl-methoxycarbonylamino)-methyl]-benzoylamino}-ethoxy)-ethoxy]-ethyl}-carbamic Acid Tert-Butyl Ester The general DIC coupling procedure was followed in THF, the compound, 4 was isolated using flash chromatography (particle size 32-63 μm) with 100% EA TLC (100% EA $R_f$: 0.23) (35% yield); ESIMS: (M+H)+ Calcd, 603.3; Found, 604.3. $H^1$ NMR (200 MHz, $CDCl_3$) 7.74-7.26 (m), 6.7 (s, 1H), 5.3 (s, 1H) 3.7-4.0 (m), 3.2 (m, 3H) 1.4 (s, 9H), 1.0 (s, 7H).

Fmoc Cleavage of 4

Fmoc cleavage was performed in 10% piperidine and dichloromethane with stirring at room temperature, the reaction progress was monitored by TLC. The reaction time was 2.5 hrs. The solvent was removed in vacuo. The compound, 4a was isolated using flash chromatography (particle size 32-63 μm) with a 100% EA—1:20 EA:MeOH (with 1% triethylamine) gradient (80% yield). ESIMS:(M+H)+ Calcd, 381.2; Found, 382.2.

Synthesis of {2-[2-(2-{4-[(4,6-Dichloro-[1,3,5]triazin-2-ylamino)-methyl]-benzoylamino}-ethoxy)-ethoxy]-ethyl}-carbamic Acid Tert-Butyl Ester (AM)

The general cyanuric chloride coupling procedure was followed for the intermediate linker 4a. (100% dichloromethane:Acetone $R_f$ 5:1=0.21). The product, AM was isolated using flash chromatography (particle size 32-63 μm) with a dichloromethane:Acetone 5:1—dichloromethane:Acetone 3:1 gradient. The product was an orange oil (52% yield). TLC (dichloromethane:acetone 5:1, $R_f$=0.21) ESIMS: (M+H)+ Calcd, 528.1; Found, 529.1. $H^1$ NMR (200 MHz, $CDCl_3$) δ 7.6-7.8 (d, 2H, J=4 Hz) 7.35-7.37 (d, 2H, 4 Hz), 6.7-6.8 (m, 2H) 4.9 (s, 1H), 4.72 (d, 2H, J=4 Hz,) 3.5-3.7 (m) 3.2 (m, 2H) 1.8 (s, 2H) 1.4 (s, 9H).

General Procedure for Coupling Building Block I and Building Block II

Building Block II (0.44 mmole) was added to Building Block I (0.11 mmole) in DIEA (1 mL) and anhydrous THF (10 mL) at room temperature. The reaction mixture was heated to 60° C. for 3 hr and filtered. The resin was washed with DMF (5 times), alternatively with dichloromethane and methanol (5 times), and finally dichloromethane (5 times). The resin was dried in vacuum.

General Procedure for the Final Amination on the Resin and Product Cleavage

Desired amines (4 equiv.) were added to the resin (10 mg), coupled with Building Block I and Building Block II, in DIEA (8 μL) and 1 mL of NMP:n-BuOH (1:1). The reaction mixture was heated to 120° C. for 3 hr. The resin was washed with DMF (5 times), alternatively with dichloromethane and methanol (5 times), and finally dichloromethane (5 times). The resin was dried in vacuum.

The product cleavage reaction was performed using 10% trifluoroacetic acid (TFA) in dichloromethane (1 mL) for 30 min at room temperature and washed with dichloromethane (0.5 mL).

Free hydroxyl containing compounds were further treated with a piperazine resin in 0.5 ml THF at room temperature for 5 hrs to cleave the trifluoroacetic ester that was formed upon treatment with TFA. The resin was filtered out and washed with 0.1 ml THF.

The purity and identity of all the products were monitored by LC-MS at 250 nm (Agilent 1100 model); more than 90% of compounds demonstrated >90% purity.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCES (1) (a) Lokey, R. S. *Curr Opin Chem Biol* 2003, 7, 91-96; Tan, D. S. *Nature Biotechnology* 2002, 20, 561-563.

(b) Specht, K. M.; Shokat, K. M. *Curr Opin Cell Biol* 2002, 14, 155-159.

(c) Schreiber, S. L. *Chem. Eng. News* 2003, March 3, pp 51-61.

(2) (a) Jung, G. *Combinatorial chemistry: synthesis, analysis, screening*; Wiley-VCH: Weinheim; Cambridge, 1999.

(b) Nicolaou, K. C.; Hanko, R.; Hartwig, W. *Handbook of Combinatorial Chemistry: Drugs, Catalysts, Materials*; Wiley-VCH: Weinheim, 2002.

(3) (a) Chang, Y. T.; Choi, G.; Bae, Y. S.; Burdett, M.; Moon, H. S.; Lee, J. W.; Gray, N. S.; Schultz, P. G.; Meijer, L.; Chung, S. K.; Choi, K. Y.; Suh, P. G.; Ryu, S. H. *Chembiochem* 2002, 3, 897-901.

(b) Verdugo, D. E.; Cancilla, M. T.; Ge, X.; Gray, N. S.; Chang, Y. T.; Schultz, P. G.; Negishi, M.; Leary, J. A.; Bertozzi, C. R. *J Med Chem* 2001, 44, 2683-2686.

(c) Armstrong, J. I.; Portley, A. R.; Chang, Y. T.; Nierengarten, D. M.; Cook, B. N.; Bowman, K. G.; Bishop, A.; Gray, N. S.; Shokat, K. M.; Schultz, P. G.; Bertozzi, C. R. *Angew Chem Int Edit* 2000, 39, 1303-1306.

(d) Rosania, G. R.; Chang, Y. T.; Perez, O.; Sutherlin, D.; Dong, H. L.; Lockhart, D. J.; Schultz, P. G. *Nat Biotechnol* 2000, 18, 304-308.

(e) Chang, Y. T.; Gray, N. S.; Rosania, G. R.; Sutherlin, D. P.; Kwon, S.; Norman, T. C.; Sarohia, R.; Leost, M.; Meijer, L.; Schultz, P. G. *Chemistry & Biology* 1999, 6, 361-375.

(f) Gangjee, A.; Yu, J.; Kisliuk, R. L.; Haile, W. H.; Sobrero, G.; McGuire, J. J. *J Med Chem* 2003, 46, 591-600.

(g) Baraldi, P. G.; Cacciari, B.; Spalluto, G.; Bergonzoni, M.; Dionisotti, S.; Ongini, E.; Varani, K.; Borea, P. A. *J Med Chem* 1998, 41, 2126-2133.

(h) Baraldi, P. G.; Cacciari, B.; Romagnoli, R.; Spalluto, G.; Monopoli, A.; Ongini, E.; Varani, K.; Borea, P. A. *J Med Chem* 2002, 45, 115-126.

(4) Moon, H. S.; Jacobson, E. M.; Khersonsky, S. M.; Luzung, M. R.; Walsh, D. P.; Xiong, W. N.; Lee, J. W.; Parikh, P. B.; Lam, J. C.; Kang, T. W.; Rosania, G. R.; Schier, A. F.; Chang, Y. T. *J Am Chem Soc* 2002, 124, 11608-11609.

(5) Bork, J. T.; Lee, J. W.; Khersonsky, S. M.; Moon, H. S.; Chang, Y. T. *Org Lett* 2003, 5, 117-120.

(6) Peterson, R. T.; Link, B. A.; Dowling, J. E.; Schreiber, S. L. *P Natl Acad Sci USA* 2000, 97, 12965-12969.

(7) (a) SaeboeLarssen, S.; Lambertsson, A. *Genetics* 1996, 143, 877-885.

(b) Wool, I. G. *Trends Biochem Sci* 1996, 21, 164-165.

(c) Saeboe-Larssen, S.; Lyamouri, M.; Merriam, J.; Oksvold, M. P.; Lambertsson, A. *Genetics* 1998, 148, 1215-1224.

(d) Weijers, D.; Franke-van Dijk, M.; Vencken, R. J.; Quint, A.; Hooykaas, P.; Offringa, R. *Development* 2001, 128, 4289-4299.

(8) Golling, G.; Amsterdam, A.; Sun, Z. X.; Antonelli, M.; Maldonado, E.; Chen, W. B.; Burgess, S.; Haldi, M.; Artzt, K.; Farrington, S.; Lin, S. Y.; Nissen, R. M.; Hopkins, N. *Nat Genet* 2002, 31, 135-140.

What is claimed is:

1. A method for synthesizing a tagged 1,3,5-triazine library comprising:
    assembling three building blocks prepared separately, wherein at least one of the building blocks is coupled to a 4-formyl-3,5-dimethoxyphenoxymethyl resin and assembled orthogonally;
    wherein at least one of the building blocks carries a linker, wherein the linker is attached to the building block at a first end of the linker, so that each library compound contains a linker at the triazine moiety connected to the first end, and
    separating the tagged triazine compounds are separated from the resin;
    wherein a second end of the linker carries a label; and
    wherein the label is selected from the group consisting of azide, amino, NHBoc, acetylene, or fluorescent moieties.

2. The method according to claim 1 wherein the linker is a triethyleneglycol, alkyl or aryl moiety.

3. A method for preparing a tagged triazine library comprising:
    a. adding an amine or an amino alcohol to a suspension of a 4-formyl-3,5-dimethoxyphenoxylmethyl resin to form a first building block on the resin;
    b. reacting cyanuric chloride with an amino-terminated linker in a separate container to form a second building block;
    c. mixing the first building block with the second building block and coupling the first building block to the second building block to form a coupled building block;
    d. adding an amine to react with a chloride on the first building block of the coupled building block to form a tagged triazine compound coupled to a 4-formyl-3,5-dimethoxyphenoxylmethyl resin; and
    e. cleaving the tagged triazine compound from the resin.

4. The method according to claim 3 wherein an end group of the linker carries moieties selected from the group consisting of azide, amino, NHBoc, biotin, acetylene, and fluorescent groups.

* * * * *